(12) United States Patent
Preuss

(10) Patent No.: US 8,877,819 B2
(45) Date of Patent: Nov. 4, 2014

(54) METHODS FOR TREATING HEAT STRESS AND RELATED COMPOSITIONS

(75) Inventor: Harry George Preuss, Fairfax Station, VA (US)

(73) Assignee: Georgetown University, Washington, DC (US)

( * ) Notice: Subject to any disclaimer, the term of this patent is extended or adjusted under 35 U.S.C. 154(b) by 431 days.

(21) Appl. No.: 13/122,362

(22) PCT Filed: Sep. 29, 2009

(86) PCT No.: PCT/US2009/058718
§ 371 (c)(1),
(2), (4) Date: May 13, 2011

(87) PCT Pub. No.: WO2010/039676
PCT Pub. Date: Apr. 8, 2010

(65) Prior Publication Data
US 2011/0217389 A1    Sep. 8, 2011

Related U.S. Application Data

(60) Provisional application No. 61/102,290, filed on Oct. 2, 2008.

(51) Int. Cl.
*A61K 31/122* (2006.01)
*A61K 33/24* (2006.01)
*A61K 38/01* (2006.01)

(52) U.S. Cl.
CPC .................................. *A61K 31/122* (2013.01)
USPC ............................ 514/691; 424/655; 514/1.1

(58) Field of Classification Search
CPC ... A61K 31/122; A61K 33/24; A61K 38/018; A61K 2300/00
USPC ..................................... 514/691, 1.1; 424/655
See application file for complete search history.

(56) References Cited

U.S. PATENT DOCUMENTS

| 5,863,953 | A  | 1/1999 | Luddecke et al. |
| 6,344,214 | B1 | 2/2002 | Lorenz |
| 2007/0003502 | A1 | 1/2007 | Tanabe et al. |
| 2007/0196496 | A1 | 8/2007 | Farber et al. |
| 2008/0089941 | A1 | 4/2008 | Mower |

OTHER PUBLICATIONS

ScienceDaily, Nov. 1, 2007, obtained from the web at http://www.sciencedaily.com/videos/2007/1108-sunscreen_in_a_pill.htm on May 20, 2013.*
International Search Report for PCT/US09/58718 mailed Jan. 13, 2010.

* cited by examiner

*Primary Examiner* — John Pak
*Assistant Examiner* — Nathan W Schlientz
(74) *Attorney, Agent, or Firm* — Kilpatrick Townsend & Stockton, LLP

(57) ABSTRACT

Methods of treating, reducing, and/or preventing heat stress are provided. For example, provided is a method of treating or preventing heat stress in a subject comprising selecting a subject in need of heat stress treatment or prevention and administering an effective amount of one or more of astaxanthin and milk casein hydrolysate, or a derivative thereof to the subject. Also provided are methods of reducing the effects of a fever in a subject comprising administering an effective amount of one or more of astaxanthin, chromium and milk casein hydrolysate, or a derivative thereof, to the subject. Also provided are pharmaceutical compositions, comprising astaxanthin and one or more of chromium or milk casein hydrolysate.

17 Claims, 6 Drawing Sheets

METHODS FOR TREATING HEAT STRESS AND RELATED COMPOSITIONS

CROSS REFERENCE TO RELATED APPLICATIONS

This application claims the benefit of U.S. Provisional Application No. 61/102,290, filed Oct. 2, 2008, which is incorporated by reference in its entirety as part of this application.

BACKGROUND

Heat stress is a dangerous condition that can detrimentally affect humans and animals. High air temperatures, high fevers, radiant heat sources, high humidity, direct physical contact with hot objects, or strenuous physical activities are examples of factors that have a high potential for inducing heat stress.

SUMMARY

Methods of treating, reducing, and/or preventing heat stress are provided. For example, provided is a method of treating or preventing heat stress in a subject comprising selecting a subject in need of heat stress treatment or prevention and administering an effective amount of one or more of astaxanthin and milk casein hydrolysate, or a derivative thereof to the subject. Also provided are methods of reducing the effects of a fever in a subject comprising administering an effective amount of one or more of astaxanthin, chromium and milk casein hydrolysate, or a derivative thereof, to the subject. Also provided are pharmaceutical compositions, comprising astaxanthin and one or more of chromium or milk casein hydrolysate.

DETAILED DESCRIPTION

Figure 1:
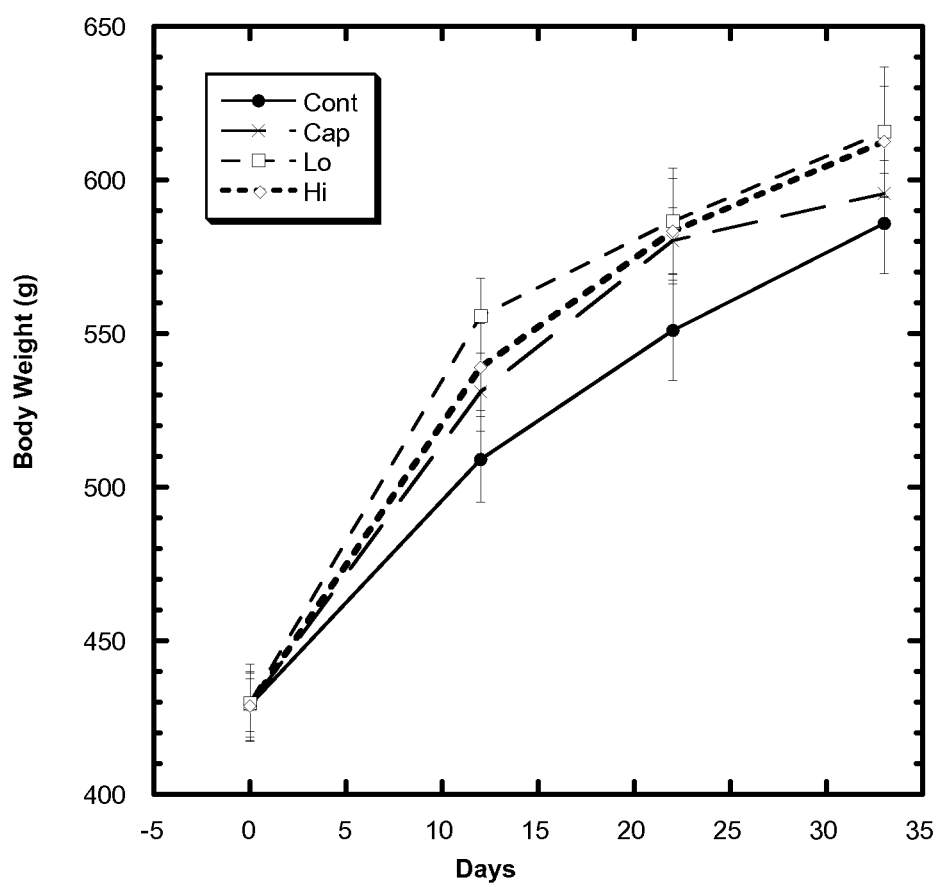
FIG. 1 is a graph showing body weight measurements (grams) over time (days).

Methods of treating, reducing, and/or preventing heat stress are provided. For example, provided is a method of treating or preventing heat stress in a subject comprising selecting a subject in need of heat stress treatment or prevention and administering an effective amount of one or more of astaxanthin and milk casein hydrolysate or a derivative thereof to the subject. An example milk casein hydrolysate that can be used is Lactium® (Pharmachem Laboratories Inc., Kearny, N.J.).

The term subject means an individual human or non-human animal. The subject may be a vertebrate, more specifically a mammal (e.g., a human, horse, pig, rabbit, dog, sheep, goat, non-human primate, cow, cat, guinea pig or rodent), a fish, a bird or a reptile or an amphibian. The subject may be an invertebrate, more specifically an arthropod (e.g., insects and crustaceans). The term does not denote a particular age or sex. Thus, adult and newborn subjects, as well as fetuses, whether male or female, are intended to be covered. The methods can be used to treat, reduce and/or prevent heat stress in human subjects or in animal subjects.

Symptoms of heat stress include, but are not limited to, hyperthermia, headache, dizziness, thirst, muscle cramps, tachycardia, oligouria, malaise, hypotension, delirium, renal failure, hyperventilation, pulmonary edema, arrhythmia, shock, lightheadedness, fainting, weakness, exhaustion, fever, moist skin, irritability, confusion, dry skin, hot skin, anhidrosis, loss of consciousness, seizures, convulsions, heat stroke, vomiting, upset stomach, and death. Beyond symptoms associated with a subject experiencing heat stress, heat stress can cause adverse sequelae. For example, a reduction in egg laying or egg quality can indicate heat stress in a species that lays eggs. Other examples of heat stress sequelae include increased lung disease in humans or cattle, or ulcers, in humans. By treating, reducing, and/or preventing heat stress in a subject, the provided methods can beneficially affect the symptoms of heat stress, and can also or alternatively reduce or eliminate any sequelae related to heat stress in a subject. Heat stress also includes heat exhaustion and heat stroke.

Symptoms of heat stress can be detected and can indicate an individual or population of individuals in need of treatment for or prevention of heat stress. Similarly, sequelae can be detected in an individual or population of individuals and can indicate an individual or population of individuals in need of treatment for or prevention of heat stress. Subjects, including individuals or populations of individuals, in need of heat stress treatment of prevention can also be determined by identifying individuals or populations with an increased likelihood of experiencing heat stress.

Individuals or populations with an increased likelihood of experiencing heat stress can have individual or environmental factors which may predispose an individual or population to heat stress. For example, a subject in need of treatment for or prevention of heat stress can be a subject that is exposed to, or is expected to be exposed to, high environmental temperatures or physical exertion. Other factors, such as, but not limited to, age and heath condition of an individual, can also predispose an individual to heat stress. For example, the elderly, infants, and those with other illnesses may be at higher risk for heat stress. For example, those older than 65 years or younger than one or two years are at a higher risk of heat stress and heat stroke. Moreover, in some geographic regions there is a seasonal increase in risk for heat stress. Such an increase can be due to increased ambient temperatures and/or humidity levels to which subjects are exposed.

Other examples include those who work, live, or are otherwise active outside during high temperature conditions. Athletes and soldiers are non-limiting examples of individuals that are likely to be subjected to high temperatures and physical exertion. Also, many production animals, such as poultry and cattle, can experience high temperature environments that can indicate a need for heat stress treatment or prevention.

Chronic disease, some medications, and poor physical condition can impair a subject's normal mechanisms of dissipating heat, which can result in heat stress or a predisposition to heat stress. Heat stress can result from a subject's inability or reduced ability to dissipate heat produced by metabolic activity, which often is associated with an increased ambient temperature. Pre-existing conditions that can contribute to heat stress include, but are not limited to alcoholism, anorexia, cardiac disease, cystic fibrosis, dehydration, diabetes insipidus, eating disorders, extremes of age, febrile illness, gastroenteritis, history of heatstroke, hypokalemia, obesity, poor acclimatization, sleep deprivation, sunburn, sweat gland dysfunction, uncontrolled diabetes, uncontrolled hypertension, thyroid disorder, and upper respiratory tract infection. Medications that can contribute to heat stress include alcohol, alpha adrenergics, anticholinergics, antihistamines, benzodiazepines, beta blockers, calcium channel blockers, neuroleptics, phenothiazine diuretics, tricyclic antidepressants. Subjects having these conditions and/or medication histories can indicate subjects in need of heat stress treatment or prevention.

An example method of determining a subject in need of heat stress treatment or prevention can include determining the heat index of the environment to which a subject has been exposed or will be exposed. Heat index accounts for relative humidity and temperature, with higher values of humidity and temperature equating to a higher heat index. The higher the heat index to which a subject has been or will be exposed indicates a greater likelihood of heat stress. For example, optionally, a subject that has been or will be exposed to a heat index of 80° F. or greater indicates a subject in need of heat stress treatment or prevention. Optionally, a subject that has been or will be exposed to a heat index of 80° F. to 90° F., 90° F. to 105° F., 105° F. to 130° F. or 130° F. or higher, indicates a subject in need of heat stress treatment or prevention. In a subject with a predisposition to heat stress, lower heat index levels could be relied upon to initiate therapy.

After a subject is identified that is in need of heat stress treatment or prevention, an effective amount of one or more of astaxanthin and milk casein hydrolysate (e.g., Lactium®), or a derivative thereof can be administered to the subject. An effective amount of chromium can also be administered to the subject.

An effective amount of astaxanthin, chromium, milk casein hydrolysate (e.g., Lactium®) or other agent described herein is a nontoxic but sufficient amount to provide the desired result. The dosages or amounts of the compositions described herein are large enough to produce the desired effect or to prevent or delay the negative outcome in the method by which delivery occurs. The effective amount can vary from subject to subject, depending on the species, age, and general condition of the subject, the severity of the heat stress or fever that is being treated or prevented, the particular agent used, its mode of administration, and the like. Thus, it is not possible to specify an exact effective amount. However, an appropriate effective amount can be determined by one of ordinary skill in the art, for example, by using the assessment techniques indicated above. The dosage should not be so large as to cause adverse side effects, such as unwanted cross-reactions, anaphylactic reactions, and the like. The dosage can be adjusted by an individual physician, veterinarian, or other medical or animal professional based on the clinical condition of the subject involved. The dose, schedule of doses, and route of administration can be varied accordingly.

Optionally, the effective amount of one or more of astaxanthin and milk casein hydrolysate (e.g., Lactium®), or a derivative thereof can be administered to the subject prior to the onset of heat stress symptoms, or prior to the conditions that increase the likelihood that the subject will experience heat stress. An effective amount of chromium can also be administered to the subject prior to the onset of heat stress symptoms, or prior to the conditions that increase the likelihood that the subject will experience heat stress.

For example, an administered effective amount of astaxanthin, chromium and milk casein hydrolysate (e.g., Lactium®), or a derivative thereof can be administered to the subject once daily. An administered effective amount of astaxanthin, chromium and milk casein hydrolysate (e.g., Lactium®) or a derivative thereof can be administered to the subject more frequently than once daily. For example, one or more of an effective amount of astaxanthin, chromium and milk casein hydrolysate (e.g., Lactium®), or a derivative thereof can be administered twice, three times or more frequently each day. An appropriate dosing regimen can be determined by one of ordinary skill in the art, for example, by using the assessment techniques indicated above. Optionally, the administration or administrations can be repeated for two or more days. For example, the administration or administrations can be repeated for days, weeks, months or years. Moreover, an administration can be given to the subject prior to, during, or after the subject being exposed to high environmental temperatures, physical exertion, or to any other factor that increases the likelihood of heat stress in that subject. For example, an administration can be repeated once or more daily every day for a week, month or year, or once or more for any subset of a week month or a year prior to, during, or after a heat stress event, or prior to that subject being exposed to conditions that increase the likelihood of a heat stress event. The administration can also be seasonal, wherein it is initiated before high seasonal temperatures and ceased at the or after such seasonal temperatures become more moderate. Thus, an effective dosage of astaxanthin, chromium and milk casein hydrolysate (e.g., Lactium®), or a derivative thereof can be administered after a heat stress event or during an acute heat stress event.

Optionally, an effective amount of astaxanthin or a derivative thereof is administered to the subject. Astaxanthin is an orange pigment that provides color to many living organisms—giving salmon, lobsters, and shrimp their reddish color upon cooking. It exhibits strong free radical scavenging activity by protecting against lipid peroxidation and oxidative damage of LDL-cholesterol, cell membranes, cells, and tissues. Astaxanthin can be administered orally to the subject. Optionally, the administered effective amount of astaxanthin or a derivative thereof is about 0.02 mg/kg or greater. For example, the administered effective amount of astaxanthin or a derivative can be about 0.14 mg/kg, 0.17 mg/kg, 0.21 mg/kg or 0.28 mg/kg or greater. Thus, the administered effective amount of astaxanthin or a derivative thereof can optionally be between about 0.02 mg/kg and about 0.28 mg/kg including any value in between. By way of example, the astaxanthin or a derivative thereof is administered in a daily dosage of or greater than 4 mg/day.

Conversions of dosages for one species to another are known. For example, the doses of astaxanthin added to rodent food can be converted to human doses based on a ratio of body weights: comparing a 500 g rat to a 70 kg human (delta=140). Surface area rather than body weight can also be used in calculating dosing. The conversion factor for surface area for a rat compared to a human is seven, which makes the delta 20 instead of 140. Thus, estimating that rats eat approximately 25 grams of food per day. Thus, at 5 mg/kg in the food, rats would eat 0.125 mg and multiplied by 20, this would approximate a human dose of 2.5 mg. At 25 mg/kg, the rats would eat five times more astaxanthin, roughly the equivalent to a human daily dose of 12.5 mg. Thus, one of skill in the art can modify and adapt the dosage of astaxanthin according to age, sex, and species.

The effective amount of astaxanthin or a derivative thereof can optionally be administered to the subject once daily. The once daily administration of an effective amount of astaxanthin or a derivative thereof can be repeated for two or more days. At least one daily administration of an effective amount of astaxanthin or a derivative thereof can be optionally given to the subject prior to the subject being exposed to high environmental temperatures or physical exertion. When using an optional daily dosing routine, the administered effective amount of astaxanthin or a derivative thereof can be about 2 mg-4 mg/day or greater to the subject. For example, the administered effective amount of astaxanthin or a derivative thereof can be between about 2 mg/day and 20 mg/day. Optionally, the administered effective amount of astaxanthin or a derivative thereof is between about 12 mg/day and 15 mg/day.

Optionally, an effective amount of chromium or a derivative thereof is administered to the subject. The chromium administered can be trivalent chromium or a derivative thereof. Chromium can be administered orally to the subject. The administered effective amount of chromium or a derivative thereof can optionally be about 100 µg/day or greater. For example, the administered effective amount of chromium or a derivative thereof can be between about 100 µg/day and about 600 µg/day. The effective amount of chromium or a derivative thereof can administered once daily to the subject for two or more days. At least one daily administration of an effective amount of chromium or a derivative thereof can be given to the subject prior to the subject being exposed to high environmental temperatures or physical exertion.

Optionally, an effective amount of astaxanthin and an effective amount of chromium are administered to the subject. An effective amount of milk casein hydrolysate (e.g., Lactium®) or a derivative thereof can also be administered to the subject. Lactium® is a milk casein hydrolysate. Milk casein hydrolysate (e.g., Lactium®) can be administered orally to the subject. The administered effective amount of milk casein hydrolysate (e.g., Lactium®) or a derivative thereof is about 1580 mg daily, but can range from 150 to 15,000 mg/day. Optionally, an effective amount of astaxanthin and milk casein hydrolysate (e.g., Lactium®), milk casein hydrolysate (e.g., Lactium®) and chromium, or milk casein hydrolysate (e.g., Lactium®), astaxanthin and chromium are administered to the subject. In the methods, the agents administered can be administered concurrently, separately, or in any other temporal combination. For example, a plurality of administered agents can be administered together in a mixture. Optionally, each administered agent can be administered individually on a given day. Moreover, each administered agent can be administered separately such that one agent is given at a particular administration time (e.g., a first day) and another agent is given at another administration time (e.g., a second day). Such agents can be given at selected times of day or under selected conditions (e.g., with or without food).

Also provided is a method of reducing the effects of a fever in a subject, comprising administering an effective amount of one or more of astaxanthin, chromium and milk casein hydrolysate (e.g., Lactium®), or a derivative thereof, to the subject. High fevers, for example in children, can cause serious adverse effects such as seizures, which may or may not be associated with heat stress. Thus, one of skill in the art can administer to the subject at risk of such side effects the disclosed agent or agents. The administration can be performed before adverse symptoms arise or after adverse symptoms arise and can be performed if a particular subject is prone to high fevers or is expected to experience a high fever.

Also provided are pharmaceutical compositions comprising astaxanthin; and one or more of chromium or milk casein hydrolysate (e.g., Lactium®). Optionally, the pharmaceutical composition comprises astaxanthin and chromium. Optionally, the pharmaceutical composition comprises astaxanthin and milk casein hydrolysate (e.g., Lactium®). Optionally, the pharmaceutical composition comprises astaxanthin, milk casein hydrolysate (e.g., Lactium®) and chromium.

Astaxanthin, chromium, milk casein hydrolysate (e.g., Lactium®), or combinations thereof can be administered to the subject in a number of ways including entrally (e.g. orally) and parentrally (e.g. intravenous injection). Thus, for example, a described agent can be administered intravenously, subcutaneously, topically, sublingually, transdermally, intramuscularly, encapsulated in liposomes or microspheres, as an ophthalmic solution and/or ointment to the surface of the eye, as a nasal spray, as a nebulized solution, a powder, a solution, an emulsion, mixed or combined with food or drink, with food or drink, or as an aerosol to the nasal cavities or airways. Moreover, a described agent can be administered to a subject vaginally, rectally, intranasally, orally, by inhalation, or by intubation. Optionally, a described agent can be administered by intravenous, subcutaneous, intramuscular, or intraperitoneal injection.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the scope except as and to the extent that they are included in the accompanying claims. Efforts have been made to ensure accuracy with respect to numbers (e.g., amounts, temperature, etc.), but some errors and deviations should be accounted for.

Material and Methods

For two experiments, a total of 96 Zucker Fatty Rats (ZFR) (Charles River, Wilmington, Mass.) were used: 48 in each experiment were divided into four groups of 12 rats. Initial body weights ranged between 434 and 624 g in the first experiment and between 388 and 520 g in the second. All rats consumed a regular rat diet in crushed form (Purina Rat Chow, Ralston Purina, St. Louis, Mo.). Sucrose was added to the pulverized regular rat chow (30%, w/w). The four groups comprised a control eating the described diet and three test groups eating the same diet but with the addition of captopril or astaxanthin (two different doses). Captopril was added to the feed at 30 mg/kg, astaxanthin at 5 mg/kg to the feed of the group designated as Lo Asta, and astaxanthin at 25 mg/kg to the feed of the group designated as Hi Asta. The amount of astaxanthin added was based on 2% (w/w) content of astaxanthin to powder. The first study continued for 57 days while the second continued for 75 days.

Body Weight (BW)

BW was estimated by routine scale measurements. Two readings taken at least 10 minutes apart on a given day had to be within two grams of each other or the procedure was repeated until the weight measurements were within this range. Water and food intakes were estimated by subtracting the volume or weight of the remaining fluid and food from the amounts premeasured 24 hours earlier.

Systolic Blood Pressure (SBP)

SBP was measured by tail plethysmography using two different instruments. As in many previous studies, an instrument from Narco Biosciences (Houston, Tex.) was used. This allowed for rapid measurement SBP with a beeper sound system. The second reading was performed on an instrument obtained from Kent Scientific Corporation (Torrington, Conn.). The latter is a computerized, non-invasive tail cuff acquisition system that utilizes a specially-designed differential pressure transducer to non-invasively measure the blood volume in the tail. This instrument not only records SBP, but also provides measurements of mean blood pressure (MBP), diastolic blood pressure (DBP), and cardiac rate. The two instruments were used interchangeably. Previous experience has shown that the SBP readings were virtually the same by either instrument. Rats were allowed free access to their diet and water until SBP readings were obtained between 13.00 h and 17.00 h after a slight warming. Multiple readings on individual rats were taken. To be accepted, SBP measurements on a given rat had to be stable (consistently within 5 mm Hg).

Blood Chemistries

Blood for chemical analysis was obtained at the end of the study following removal of food four hours earlier. Blood chemistry values were obtained via dry chemistry procedures using a Johnson and Johnson (Langhorne, Pa.) Vitros® 250 instrument.

Intraperitoneal Glucose Tolerance Test (ipGTT)

During the ipGTT, glucose (2.5 g/kg BW) was injected intraperitoneally (i.p.) to challenge the tolerance to glucose. Drops of blood were obtained from the tail at 0, 30, 60, 120, 180 and 240 minutes post injection. Glucose was estimated using commercial glucose strips (Lifescan, One Touch Ultra, Melitas, Calif.).

Insulin Challenge Testing (ICT)

Testing was commenced after 17-19 hours of food deprivation. For ICT, 0.6 unit of regular insulin/kg BW (Eli Lilly Co., Indianapolis, Ind.) was administered, and blood for glucose determination was obtained from the tail vein at 7.5 min after injection. Glucose was estimated using commercial glucose strips (Lifescan, One Touch Ultra, Melitas, Calif.).

Losartan Challenge

After performing baseline SBP readings, SHR from all dietary groups were given 40 mg/kg losartan orally via gastric lavage. Three and six hours after lavage, SBP was remeasured. The decreased SBP after losartan was used to estimate activity of the RAS.

Serum Angiotensin-2 Levels

Serum angiotensin-2 was trapped by octylminicolumns (Amprep-C8, 500 mg, Amersham, Buckingshire, UK). Each minicolumn was prewashed with 5 mL of 100% methanol and then with 10 mL of 0.1% trifluoroacetic acid (TFA) in distilled water. After the serum was passed through the minicolumn, it was washed with 0.1% TFA again. The trapped peptides were eluted with 3 mL of methanol/water/TFA (80:19.9:0.1%, v/v/v). Samples were collected and dried in a vacuum centrifuge and dissolved in 0.1M Tris-acetate buffer (pH 7.4) containing 2.6 mM disodium salt of ethylenediaminetetraacetic acid (EDTA), 1 mM phenylmethylsulphonyl fluoride, and 0.1% bovine serum albumin.

Angiotensin-2 was measured by radioimmunoassay using an angiotensin-2 antibody (Peninsula Laboratories Inc., Belmont, Calif.). The sensitivity of the assay is 1.0 pg/tube. The 500-fold diluted angiotensin-2 antibody (100 μL) was added to the sample (400 μL) and standard tubes that were incubated 24 hours at 4° C. The ([3-$^{125}$I] iodotyrosyl) angiotensin-2 (Peninsula) 100 μL was reconstituted in 0.1M Tris-acetate buffer and was added to each tube at a concentration of approximately 15,000 cpm with further incubation 24 hours at 4° C. On the third day, 300 μL of 1.25% bovine-albumin was added to each tube and mixed, and 800 μL of 25% polyethylene glycol 8,000 was added and mixed once again. After centrifugation at 1,500 g for 30 min at 4° C., the supernatant was aspirated and the pellet was counted with a gamma-counter.

Serum Angiotensin Converting Enzyme (ACE) Activity

Serum ACE activity was measured by a commercial kit (Sigma Co. Ltd, St. Louis, Mo.). This spectrophotometric method utilizes the synthetic tripeptide substrate N-[3-(2-furyl)acryloyl]-phenylalanylglcylglcine (FAPGG). FAPGG is hydrolyzed by ACE to furylacryloylphenylalanine (FAP) and glycylglycine. Hydrolysis of FAPGG results in a decreased absorbency at 340 nm. Serum ACE activity was determined by comparing the sample reaction rate to that obtained with an appropriate ACE calibrator.

Cytokine Assay

Various cytokines were measured by ELISA methodology using kits from the following sources: rat MCP-1—Assay Designs Inc., Ann Arbor, Mich.; rat adiponectin—ALPCO Diagnostics, Salem, N.H.; TNF-a, ALPCO Diagnostics, Salem, N.H.; RAT IL-1B—Assay Designs Inc, Ann Arbor, Mich.; RAT IL-6—ALPCO Diagnostics, Salem, N.H.

Organ Weights

Organ weights were measured immediately after sacrifice of the rats.

Lipid Peroxidation and DNA Fragmentation

Assessment of Lipid Peroxidation:

Thiobarbituric acid-reactive substances (TBARS) as an index of lipid peroxidation were determined on hepatic and kidney homogenates from control and treated and malondialdehyde (MDA) was used as the standard. Absorbance values were measured at 535 nm and an extinction coefficient of $1.56 \times 10^5$ $M^{-1}$ $cm^{-1}$ was used.

Assessment of DNA Fragmentation:

Frozen liver and kidney samples were homogenized in lysis buffer (5 mM Tris-HCl, 20 mM EDTA, 0.5% Triton X-100, pH 8.0). Homogenates were centrifuged at 27,000 g for 20 min to separate intact chromatin in the pellet from fragmented DNA in the supernatant fraction. Pellets were re-suspended in 0.5 M perchloric acid and 5.5 M perchloric acid was added to supernatant samples to reach a concentration of 0.5 M. Samples were heated at 90° C. for 15 min and centrifuged at 1,500 g for 10 min to remove protein. Resulting supernatants were reacted with diphenylamine for 16-20 h at room temperature. Absorbance was measured at 600 nm. DNA fragmentation in control samples was expressed as percentage of total DNA appearing in the supernatant fraction. Treatment effects are reported as percent of control fragmentation.

Statistical Analyses

Results are presented as mean±SEM. SBP and BW were examined by repeated measures, 2-way analyses of variance (one factor being group and the second factor being time of examination). Where a significant effect of regimen was detected by ANOVA (p<0.05), the Dunnett t test was used to establish which differences between means reached statistical significance. Other measurements were assessed by one-way analyses of variance. Statistical significance was set at a p<0.05.

Results

Experiment 1

Body Weight (BW)

As shown in FIG. 1, over the initial 33 days of the first study, BW increased slightly over control in the test groups, i.e., ZFR receiving captopril, and low (Lo) and high (Hi) levels of astaxanthin, although these differences did not reach statistical significance at any timed measurements.

Food and Water Intake

After three weeks on the various regimens, average food and water intake were similar in all groups. The possible exception was in the captopril group that showed a trend toward increased water intake.

Systolic Blood Pressure (SBP)

Figure 2:
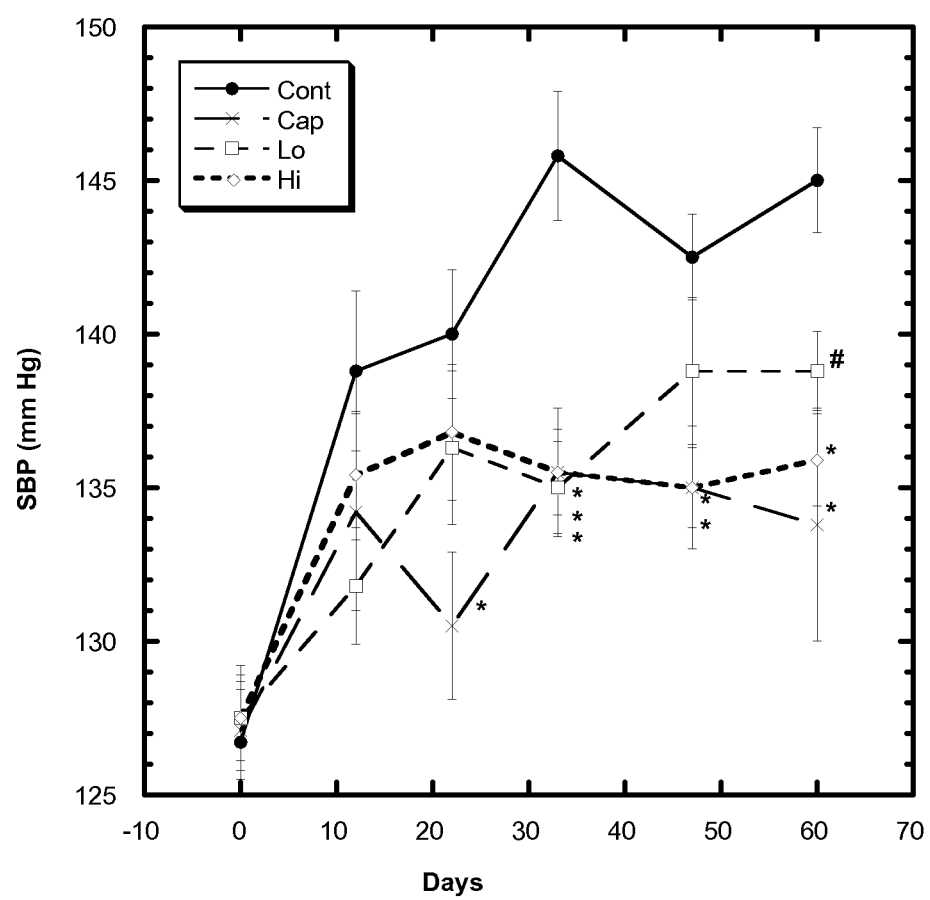
FIG. 2 is a graph showing systolic blood pressure measurements (mmHg) over time (days).

As shown in FIG. 2, during the first month, the SBP of the control group rose steadily from the initial reading of 126.7 mm Hg±1.7 (SEM) to 145.8 mm Hg±2.1 (SEM) and remained around this level until the end of study. On the 33$^{rd}$ day, all BPs of the test groups were significantly lower than those of control. The captopril and Hi Astaxanthin groups showed a significantly lower SBP over the last month; while there was a tendency for the SBP to be lower in the Lo Asta group.

Heat Stress

On the 42$^{nd}$ day, the temperature of rodent quarters rose from 72° F. to the range of 86-89° F. It was estimated that the rats were exposed to this elevated temperature for 5-6 hours. By the time the rats were removed from the heat, approximately one third each of the control (4/12), captopril (4/11) and Lo Asta (4/12) groups survived. In contrast all ZFR in the Hi Asta group survived (11/11).

Tests after Heat Stress

Twelve days after the heat stress, the average increase in BW among the surviving rats was not statistically different. The average SBP of the captopril and Hi Asta groups remained statistically lower than the control. Although the average SBP was lower than control in the Lo Asta group, this value was not statistically significant from the control. In the following week, two additional tests were run on the survivors. Compared to the control, SBP decreased significantly less after losartan challenge in the Hi Asta group, showed a trend toward a lesser decrease in the captopril group, but was not significantly different in the Lo Asta group. Following an insulin challenge (ICT), the decreases in circulating glucose levels were not statistically different among the groups.

TABLE 1

Changes in Systolic Blood Pressure (SBP) and Body Weight (BW) after heat stress (12 days)

| Group | # | Body weight (g) | SBP (mm Hg) | Insulin (mg/dL) | Losartan |
|---|---|---|---|---|---|
| Control | 4 | 36.5 ± 7.8 | 146.3 ± 1.3 | −8.8 ± 3.0 | 39.0 ± 2.4 |
| Captopril | 4 | 37.0 ± 18.4 | 133.8 ± 2.4* | −9.8 ± 3.5 | 29.0 ± 2.4# |
| Lo Asta | 4 | 14.5 ± 13.2 | 140.0 ± 2.0 | −8.5 ± 4.1 | 38.0 ± 3.2 |
| Hi Asta | 11 | 24.3 ± 6.8 | 133.5 ± 1.5* | −7.6 ± 2.5 | 28.0 ± 2.5* |
| ANOVA (p) | | 0.51 | 0.0005 | 0.97 | 0.020 |

Trend toward significance;
*Statistically significant line. Although not statistically different due to the wide range of readings, rats from the Hi Asta group had a higher average baseline glucose level (406 mg/dL.±40.8 [SEM]) compared to the control (300 mg/dL.±29.8 [SEM]), the captopril (302 mg/dL.±46.1 [SEM]), and the Lo Asta (346 mg/dL.±36.5 [SEM]) groups. Examining the area under the curve after glucose challenge for the four groups of six rats, the animals in the Hi Asta group had a statistically significant lower average reading than control. Baseline insulin concentrations were: control (0.92 ng/mL±0.09 [SEM]), captopril (0.82 ng/mL±0.06 [SEM]), Lo Asta (0.80 ng/mL±0.08 [SEM]), and Hi Asta (0.90 ng/mL.±0.07 [SEM]). One hour after the glucose challenge, the insulin concentrations were: control (2.50 ng/mL±0.22 [SEM]), captopril (2.37 ng/mL±0.14 [SEM]), Lo Asta (2.15 ng/mL±0.14 [SEM]), and Hi Asta (2.23 ng/mL.±0.14 [SEM]).

Insulin Challenge Test (ICT)

Figure 4A:
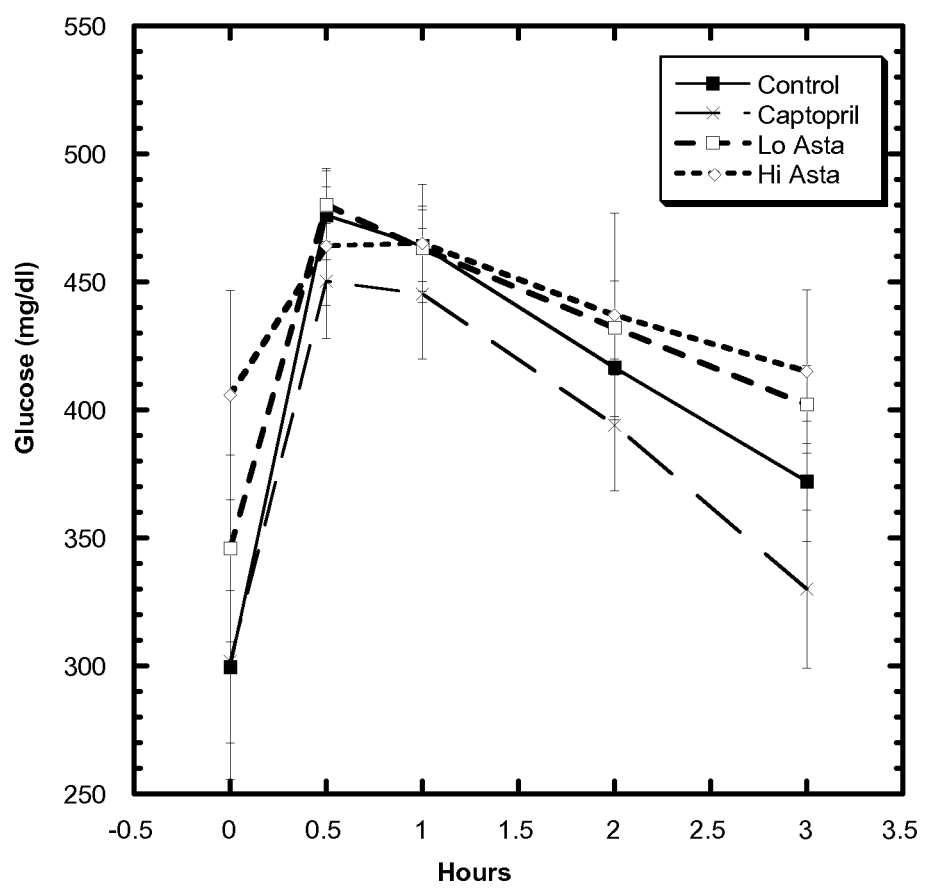
FIG. 4a is a graph showing blood glucose measurements (mg/dl) over time (hours).
Figure 4B:
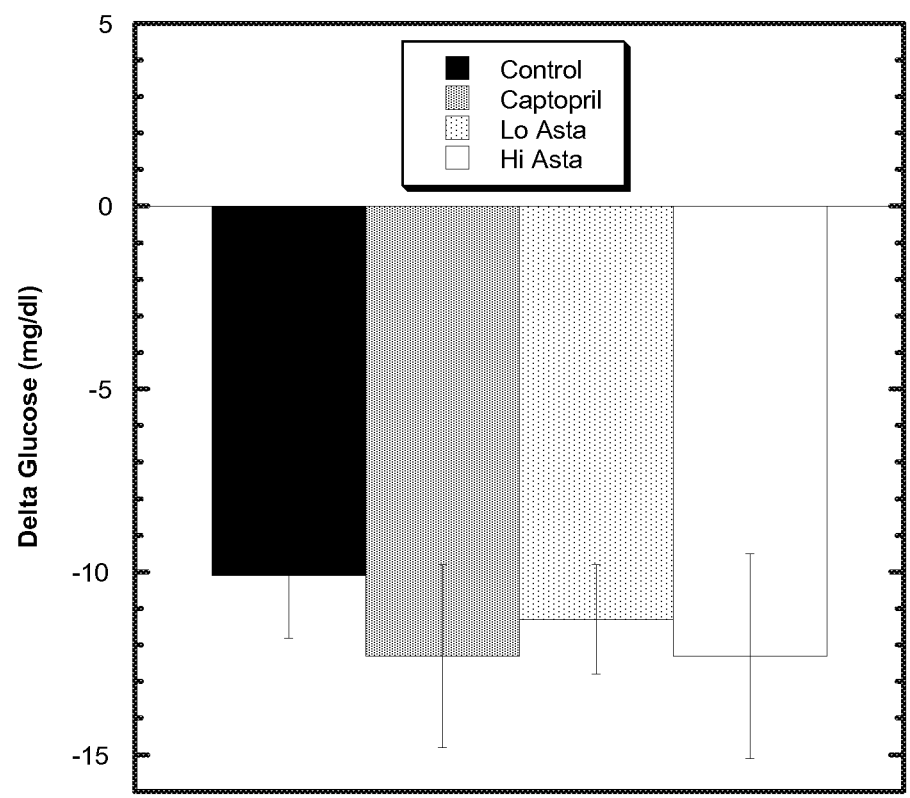
FIG. 4b is a histogram showing glucose measurements (mg/dl) after insulin challenge.

As shown in FIG. 4b, seven and one half minutes after i.p. challenge with 4 units of regular insulin, the average decrease in circulating glucose showed no significant difference among all groups.

Systolic Blood Pressure (SBP)

Figure 5:
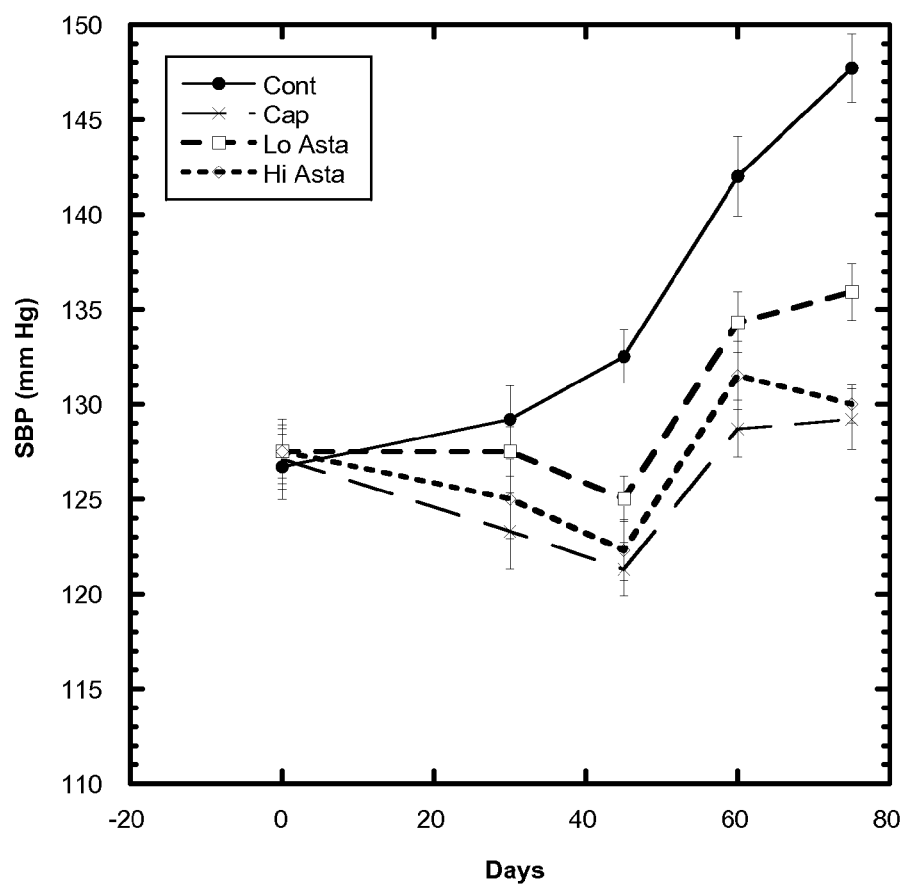
FIG. 5 is a graph showing systolic blood pressure measurements (mm Hg) over time (days).

As shown in FIG. 5, by 40 days, the average SBP of the three test groups (captopril, Lo Asta and Hi Asta were statistically significantly different, remaining significantly lower than control throughout the rest of the study. At the end of study (75 days), the SBP of the captopril and Hi Asta groups were significantly lower than in the Lo Asta group. At 60 days, a more complete evaluation was performed as depicted in Table 4. While the SBP was lower in all the test groups, the diastolic blood pressure (DBP) was significantly lower only in the captopril and Hi Asta groups. No significant differences in cardiac rates were seen among the four groups.

TABLE 2

Cardiovascular readings at 60 days

| Parameter | Control | Captopril | Lo Asta | Hi Asta |
|---|---|---|---|---|
| SBP (mm Hg) | 142.0 ± 2.1 | 129.0 ± 1.5* | 134.0 ± 1.6* | 132.0 ± 1.8* |
| DBP (mm Hg) | 111.0 ± 2.1 | 103.0 ± 1.8* | 108.0 ± 2.1 | 102.0 ± 2.0* |
| Cardiac rate | 413.0 ± 10.0 | 393.0 ± 9.3 | 387.0 ± 8.6 | 401.0 ± 10.6 |

Average ± SEM of 12 rats is shown;
*Statistically significant compared to control.
SBP-systolic blood pressure,
DBP-diastolic blood pressure.

Experiment 2

Body Weight (BW)

Figure 3:
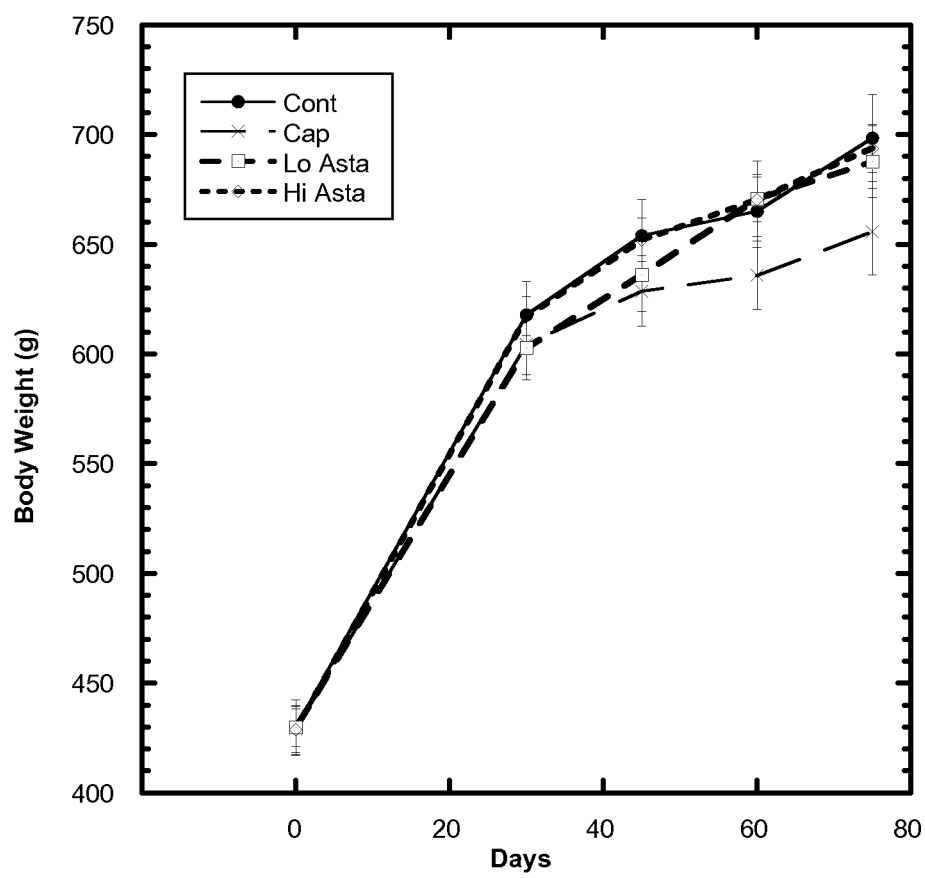
FIG. 3 is a graph showing body weight measurements (grams) over time (days).

As shown in FIG. 3, over the 11 weeks of study, the average increase in BW was not statistically different among the four groups. The control group did not show a tendency to have a lower body weight as in the first experiment.

Food and Water Intake

When food and water intake was measured at one month and two months, no statistically significant differences were seen among the groups.

Glucose Tolerance Test

As shown in FIG. 4a, ZFR had high circulating glucose levels that showed marked differences among groups at base- Evaluation of RAS System When losartan was given to each group of rats, the decrease in SBP of the three test groups was significantly less than the control. Examination of serum angiotensin converting enzyme (ACE) activity showed lesser activity in the captopril and Hi Asta groups, not in the Low Asta rats compared to control. Circulating angiotensin 2 concentrations were statistically lower in the captopril group, showed a trend toward a lower circulating level in the Hi Asta group and were not significantly different in the Lo Asta group compared to the control.

TABLE 3

Evaluation of Renin-Angiotensin System (RAS)

| Parameter | Control | Captopril | Lo Asta | Hi Asta |
|---|---|---|---|---|
| Losartan (mm Hg) | 42.5 ± 2.8 | 30.6 ± 1.8* | 33.8 ± 2.8* | 27.5 ± 1.3* |
| ACE activity (units) | 29.9 ± 1.7 | 21.5 ± 1.2* | 27.1 ± 1.4 | 24.2 ± 1.3* |
| Angio 2 (pg/mL) | 204.0 ± 12.7 | 162.0 ± 6.4* | 197.0 ± 7.2 | 177.0 ± 5.2 |

Average ± SEM of 10 rats;
*Statistical significance compared to control ($p < 0.05$);
Trend toward statistical significance ($>0.05 < 0.10$).
ACE-angiotensin converting enzyme.

Blood Chemistries

Among the values depicted, the only statistical differences and trends occurred in the blood urea nitrogen (BUN), potassium and creatinine levels in the Lo Asta group compared to control. All other chemistries seemed essentially the same in all groups.

Organ Weights

After sacrifice, the average weights of the liver, right and left kidneys and epydydimal fat pads were not significantly different among groups.

TABLE 4

Blood chemistries

| Parameter | Control | Captopril | Lo Asta | Hi Asta |
|---|---|---|---|---|
| Glucose | 320.0 ± 14.6 | 327.0 ± 23.0 | 317.0 ± 30.6 | 327.0 ± 14.2 |
| BUN | 13.8 ± 0.3 | 14.0 ± 0.5 | 25.3 ± 5.4* | 15.0 ± 0.5 |
| Creatinine | 0.5 ± 0.02 | 0.4 ± 0.02 | 0.6 ± 0.90# | 0.5 ± 0.01 |
| Sodium | 140.0 ± 0.5 | 140.0 ± 0.5 | 141.0 ± 0.7 | 142.0 ± 0.8 |
| Potassium | 5.9 ± 0.06 | 6.0 ± 0.04 | 6.5 ± 0.04 | 6.0 ± 0.13 |
| Chloride | 98.9 ± 1.3 | 98.6 ± 1.0 | 98.4 ± 0.7 | 98.9 ± 0.8 |
| $CO_2$ | 24.8 ± 1.0 | 24.1 ± 0.9 | 22.5 ± 1.0 | 23.5 ± 0.5 |
| Calcium | 11.0 ± 0.2 | 11.3 ± 0.6 | 11.3 ± 0.2 | 11.4 ± 0.1 |
| Cholesterol | 295.0 ± 20.4 | 281.0 ± 15.6 | 308.0 ± 27.8 | 314.0 ± 13.6 |
| Triglycerides | 1226.0 ± 70.5 | 1029.0 ± 73.6 | 1167.0 ± 71.6 | 1172.0 ± 51.2 |
| AST | 95.3 ± 16.9 | 93.0 ± 12.8 | 105.8 ± 20.9 | 106.1 ± 21.0 |
| ALT | 68.3 ± 8.0 | 89.4 ± 13.9 | 70.9 ± 12.4 | 86.2 ± 13.7 |
| ALP | 337.0 ± 35.6 | 333.0 ± 22.1 | 364.0 ± 33.4 | 331.0 ± 27.3 |

Average ± SEM is depicted for 10-12 rats per group;
Significantly different from control. Values are mg/dL with exception of AST (aspartate aminotransferase) and ALT (alanine aminotransferase) that are in units.
BUN-blood urea nitrogen,
ALP-alkaline phosphatase.

Cytokines

Tumor necrosis factor-alpha (TNF-α) levels were statistically lower in the captopril and Hi Asta groups and IL-6 was significantly lower in the captopril group compared to control. No significant differences were noted in circulating adiponectin levels and a trend for a lowering was noted in IL-1b-a concentrations in the captopril group compared to control. Concerning MCP-1 concentrations, captopril showed a significant lowering while the Hi Asta group showed a trend toward a lowering compared to the control.

TABLE 5

Cytokines

| Parameter | Control | Captopril | Lo Asta | Hi Asta |
|---|---|---|---|---|
| TNF-α | 383.0 ± 10.2 | 242.0 ± 13.6* | 349.0 ± 11.9 | 294.0 ± 13.0* |
| IL-6 | 483.0 ± 30 | 391.0 ± 12* | 470.0 ± 21 | 433.0 ± 9.3 |
| Adiponectin | 3.92 ± 0.35 | 4.27 ± 0.39 | 4.11 ± 0.27 | 4.03 ± 0.40 |
| IL-1B-α | 488.0 ± 24.7 | 416.0 ± 14.8# | 490.0 ± 21.7 | 440.0 ± 25.5 |
| MCP-1 | 112.0 ± 6.7 | 81.0 ± 4.1* | 110.0 ± 5.2 | 96.0 ± 4.1# |

Average ± SEM of 11-12 rats;
*Statistical significance compared to control ($p < 0.05$);
Trend toward statistical significance ($>0.05 < 0.10$)

TABLE 6

Organ weights

| Group | Control | Captopril | Lo Asta | Hi Asta |
|---|---|---|---|---|
| Liver | 41.2 ± 2.1 | 43.1 ± 2.0 | 40.4 ± 2.4 | 43.3 ± 2.3 |
| Kidney (right) | 2.4 ± 0.10 | 2.3 ± 0.09 | 2.5 ± 0.34 | 2.5 ± 0.10 |
| Kidney (left) | 2.3 ± 0.11 | 2.3 ± 0.09 | 2.5 ± 0.16 | 2.4 ± 0.08 |
| Epidydimal fat pad | 22.1 ± 1.5 | 19.1 ± 1.2 | 19.3 ± 0.9 | 21.7 ± 12 |

Average ± SEM of 10-12 rats are shown.

MDA and DNA Fragmentation

Lipid peroxidation in the liver and kidneys was significantly less than control in the captopril and Hi Asta groups. In the Lo Asta group, the decrease was significant in the kidneys but showed only a trend toward a lowering in the liver. DNA fragmentation was not different among the groups.

TABLE 7

Lipid peroxidation and DNA fragmentation
data in liver and kidney tissues of rats

| | Liver | Kidney |
|---|---|---|
| Lipid peroxidation (nmoles MDA/mg protein) | | |
| Control | 5.4 ± 0.45 | 6.2 ± 0.39 |
| Captopril | 4.0 ± 0.29* | 3.4 ± 0.44* |
| Lo Asta | 4.7 ± 0.53# | 3.9 ± 0.48* |
| Hi Asta | 3.9 ± 0.46* | 3.5 ± 0.30* |
| DNA Fragmentation (% Control) | | |
| Control | 4.0 ± 0.26 (100%) | 4.3 ± 0.62 (100%) |
| Captopril | 4.0 ± 0.17 (100%) | 4.5 ± 0.51 (105%) |
| Lo Asta | 4.3 ± 0.38 (108%) | 4.4 ± 0.37 (102%) |
| Hi Asta | 4.1 ± 0.33 (103%) | 4.3 ± 0.48 (100%) |

Average ± SEM for each group of eight rats are depicted.
*Statistically different from Control ($p < 0.05$).
Significantly different from Picolinate.
MDA-malondialdehyde.

On a hot summer day, the air conditioning system in the animal quarters ceased functioning. The internal temperature of the animal quarters rose to a Fahrenheit range in the high 80's. Due to this heat stress, several ZFR that had already undergone almost six weeks of study expired. Interestingly, the ZFR in this study were the only rats in the entire animal quarters that died from the heat. This can be attributed to poor stress handling of ZFR. The following survival percentages were found among the four groups: control 4/12 (33%), captopril 4/11 (36%), lo asta 4/12 (33%) and hi asta 11/11 (100%).

Prior to the accident, the average food and water intake and weight gain were essentially the same among the four groups; and the average SBP was lower in all test groups compared to the control, although the Lo Asta group appeared to have a return of SBP toward control values as the study progressed. Following the acute stress, the surviving rats seemed to recover fully. The consistent weight gain and SBP levels continued in the same fashion as previous to the accident, i.e. SBP in the captopril and Hi Asta groups still remained significantly lower, whereas average SBP in the Lo Asta group approached that of control and was not significantly different. In the survivors, the test for insulin sensitivity showed no differences among the four groups. In contrast, the losartan challenge showed significant differences among groups even with the lesser number of ZFR to study. Compared to the control, the lower values in the Hi Asta group showed a significant difference, a trend was seen in the captopril group (positive control). Differently the Lo Asta group was similar to the control. All this indicated that astaxanthin and captopril were decreasing the activity of the RAS—astaxanthin in a dose-dependent manner.

In a second repeat study necessitated by the mishap, many of the original findings were confirmed. However, this time the captopril group seemed to lag somewhat instead of the control group. The pattern of SBP was virtually similar to the first experiment with all three groups showing a lowering—the Lo Asta group showed less lowering with time than the other two test groups. A new finding was that the captopril and Hi Asta groups showed a significantly lower diastolic BP as well. Cardiac rates were similar among all groups.

Activity of the RAS was estimated by examining the decrease in SBP after a challenge with the angiotensin receptor blocker, losartan. All three test groups showed a lesser decrease in SBP compared to the control, suggesting a lesser activity. When examining circulating ACE activity directly, the captopril and Hi Asta groups showed lower serum activity compared to the control. Although the activity of the Lo Asta group was lesser than the control, the differences were not significant. Captopril is a well-recognized ACE inhibitor: the results suggest that astaxanthin possesses this ability as well. Concerning the levels of circulating angiotensin 2, captopril showed significantly lower circulating concentrations, while Hi Asta showed a trend.

In addition to BP changes, astaxanthin has been reported to overcome insulin resistance, similar to other antioxidants. However, the results were inconclusive and did not substantiate this using an insulin challenge test in the first or second experiment. The results with the ipGTT, were difficult to interpret due to the wide range of the baseline blood sugars among the ZFR. Other reasons behind these differences may relate to the different species used (SHR vs. ZFR) or the dosages of astaxanthin used.

Although previous reports showed increased HDL cholesterol, decreased triglycerides, and improved adiponectin levels, the present study, did not support this. Again the rat species and dosing of astaxanthin may have played a role in the differences.

In general, the blood chemistries were similar among the groups with a single exception, evidence of renal damage occurred in three ZFR of the Lo Asta group based on the increased circulating concentrations of urea, creatinine and potassium. The explanation of this is not clear, but does not seem to be related to the astaxanthin intake as none of the ZFR in the Hi Asta group showed any evidence of elevations in the BUN and creatinine concentrations. At even higher doses of astaxanthin, other studies saw no renal damage. Examining liver and kidneys at the end of the study, corroborated previous experience that astaxanthin is a powerful antioxidant, although no effects on DNA damage were observed, unlike previous reports.

Captopril was able to significantly lower TNF-α, IL-6, and MCP-1. There was a trend toward a lowering of the proinflammatory IL-1B-α. For the Hi Asta group, the TNF-α was significantly lower while the MCP-1 showed a trend to be lower. TNF-α is a cytokine that causes tumor necrosis. Production of TNF-α is increased in persons who are obese and may be related to induction of insulin resistance. IL-α is another cytokine produced by adipose tissue that has been positively correlated with obesity, impaired glucose tolerance and insulin resistance. Levels of adiponectin were not statistically significantly different. In any case, astaxanthin has the ability to affect some cytokines and appears to possess anti-inflammatory properties.

Disclosed are materials, compositions, and components that can be used for, can be used in conjunction with, can be used in preparation for, or are products of the disclosed methods and compositions. These and other materials and methods are disclosed herein, and it is understood that when combinations, subsets, interactions, groups, etc. of these materials or steps of a method are disclosed that, while specific reference of each various individual and collective combinations and permutation of these compounds and steps may not be explicitly disclosed, each is specifically contemplated and described herein. For example, if a particular modification of a method of treating a subject having heat stress with astaxanthin is disclosed and discussed and a number of modifications that can be made to the method of treating a subject having heat stress are discussed, each and every combination and permutation of the heat stress, the astaxanthin, and the treatment method are specifically contemplated unless specifically indicated to the contrary. Likewise, any subset or combination of these is also specifically contemplated and disclosed.

Any patents or publications mentioned in the specification are indicative of the level of those skilled in the art. These patents and publications are herein incorporated by reference in their entirety to the same extent as if each individual publication was specifically and individually indicated to be incorporated by reference.

What is claimed is:

1. A method of treating heat stress in a subject, comprising
   (a) selecting a subject experiencing heat stress, and
   (b) administering an effective amount of astaxanthin to the subject.

2. The method of claim 1, wherein the effective amount treats one or more of the symptoms selected from the group consisting of hyperthermia, headache, dizziness, lightheadedness, fainting, weakness, exhaustion, fever, moist skin, irritability, confusion, dry skin, hot skin, no sweating, loss of consciousness, seizures, convulsions, heat stroke, vomiting, and upset stomach.

3. The method of claim 1, wherein the subject is exposed to high environmental temperatures or physical exertion.

4. The method of claim 1, wherein the administered effective amount of astaxanthin is about 0.02 mg/kg or greater.

5. The method of claim 4, wherein the administered effective amount of astaxanthin is about 0.14 mg/kg, 0.17 mg/kg, 0.21 mg/kg or 0.28 mg/kg or greater.

6. The method of claim 4, wherein the administered effective amount of astaxanthin is between about 0.02 mg/kg and about 0.28 mg/kg.

7. The method of claim 4, wherein the administered effective amount of astaxanthin is administered to the subject once daily.

8. The method of claim 7, wherein the once daily administration of an effective amount of astaxanthin is repeated for two or more days.

9. The method of claim 1, wherein the administered effective amount of astaxanthin is about 2 mg/day.

10. The method of claim 1, wherein the administered effective amount of astaxanthin is between about 2 mg/day and 20 mg/day.

11. The method of claim 10, wherein the administered effective amount of astaxanthin is between about 12 mg/day and 15 mg/day.

12. The method of claim 1, further comprising administering an effective amount of chromium to the subject.

13. The method of claim 12, wherein the chromium is trivalent chromium.

14. The method of claim 12, wherein the administered effective amount of chromium is about 100 μg/day or greater.

15. The method of claim 14, wherein the administered effective amount of chromium is between about 100 μg/day and about 600 μg/day.

16. The method of claim 12, wherein the effective amount of chromium is administered once daily to the subject for two or more days.

17. The method of claim 12, further comprising administering an effective amount of milk casein hydrolysate to the subject.

* * * * *